United States Patent [19]
Leone-Bay et al.

[11] Patent Number: 5,863,944
[45] Date of Patent: Jan. 26, 1999

[54] COMPOUNDS AND COMPOSITIONS FOR DELIVERING ACTIVE AGENTS

[75] Inventors: Andrea Leone-Bay, Ridgefield; David Gschneidner, Stamford, both of Conn.; Eric Wang, Yonkers; Donald J. Sarubbi, Bronxville, both of N.Y.

[73] Assignee: Emisphere Technologies, Inc., Hawthorne, N.Y.

[21] Appl. No.: 846,254

[22] Filed: Apr. 30, 1997

[51] Int. Cl.⁶ .......... A01N 37/00; A01N 37/12; C07C 229/00
[52] U.S. Cl. .......... 514/559; 514/563; 554/106; 562/455; 562/456
[58] Field of Search .......... 514/559, 563; 554/106; 562/455, 456

[56] References Cited

U.S. PATENT DOCUMENTS

| | | |
|---|---|---|
| Re. 24,899 | 11/1960 | Green . |
| 2,671,451 | 3/1954 | Bolger .......... 128/260 |
| 2,828,206 | 3/1958 | Rosenberg .......... 99/2 |
| 2,862,918 | 12/1958 | Meyer et al. .......... 260/123.5 |
| 2,868,740 | 1/1959 | Luce .......... 260/8 |
| 2,971,916 | 2/1961 | Schleicher et al. .......... 252/62.5 |
| 3,016,308 | 1/1962 | Macaulay .......... 177/37 |
| 3,052,655 | 9/1962 | Fox et al. .......... 260/78 |
| 3,057,344 | 10/1962 | Abella et al. .......... 128/2 |
| 3,076,790 | 2/1963 | Fox et al. .......... 260/78 |
| 3,170,802 | 2/1965 | Fukushima .......... 99/145 |
| 3,190,837 | 6/1965 | Brynko et al. .......... 252/316 |
| 3,474,777 | 10/1969 | Figge et al. .......... 128/2 |
| 3,491,093 | 1/1970 | Pachter et al. .......... 260/247.5 |
| 3,565,559 | 2/1971 | Sato .......... 424/37 |
| 3,567,650 | 3/1971 | Bakan .......... 252/316 |
| 3,574,832 | 4/1971 | Engel et al. .......... 424/183 |
| 3,576,758 | 4/1971 | Emrick .......... 252/316 |
| 3,687,926 | 8/1972 | Arima et al. .......... 260/112.5 |
| 3,725,113 | 4/1973 | Chang .......... 117/82 |
| 3,748,277 | 7/1973 | Wagner .......... 252/316 |
| 3,794,561 | 2/1974 | Matsukawa et al. .......... 195/29 R |
| 3,795,739 | 3/1974 | Birkmayer et al. .......... 424/274 |
| 3,816,404 | 6/1974 | Kablaoui et al. .......... 260/239.3 |
| 3,822,348 | 7/1974 | Higashi et al. .......... 424/95 |
| 3,849,550 | 11/1974 | Teitelbaum .......... 424/78 |
| 3,933,873 | 1/1976 | Love et al. .......... 260/239.3 |
| 3,937,668 | 2/1976 | Zolle .......... 252/316 |
| 3,939,253 | 2/1976 | Bodor et al. .......... 424/309 |
| 3,956,172 | 5/1976 | Saeki et al. .......... 252/316 |
| 3,962,416 | 6/1976 | Katzen .......... 424/19 |
| 3,976,773 | 8/1976 | Curran .......... 424/250 |
| 4,035,507 | 7/1977 | Bodor et al. .......... 424/311 |
| 4,048,268 | 9/1977 | Ludwig .......... 264/15 |
| 4,061,466 | 12/1977 | Sjoholm et al. .......... 23/230 B |
| 4,117,801 | 10/1978 | Dannelly et al. .......... 118/20 |
| 4,147,767 | 4/1979 | Yapel .......... 424/22 |
| 4,183,849 | 1/1980 | Hansen .......... 260/112.7 |
| 4,199,561 | 4/1980 | Roth et al. .......... 424/32 |
| 4,217,370 | 8/1980 | Rawlings et al. .......... 426/98 |
| 4,238,506 | 12/1980 | Stach et al. .......... 424/319 |
| 4,239,635 | 12/1980 | Rieder .......... 252/34 |
| 4,239,754 | 12/1980 | Sache et al. .......... 424/183 |
| 4,272,506 | 6/1981 | Schwarzberg .......... 424/8 |
| 4,289,759 | 9/1981 | Heavner et al. .......... 424/177 |
| 4,345,588 | 8/1982 | Widder et al. .......... 128/1.3 |
| 4,348,384 | 9/1982 | Horikoshi et al. .......... 424/101 |
| 4,351,337 | 9/1982 | Sidman .......... 128/260 |
| 4,352,883 | 10/1982 | Lim .......... 435/178 |
| 4,357,259 | 11/1982 | Senyei et al. .......... 252/316 |
| 4,388,304 | 6/1983 | Nyeki et al. .......... 424/177 |
| 4,393,192 | 7/1983 | Curatolo et al. .......... 528/292 |
| 4,402,856 | 9/1983 | Schnoring et al. .......... 428/402.22 |
| 4,402,968 | 9/1983 | Martin .......... 424/273 |
| 4,405,598 | 9/1983 | Brown .......... 424/45 |

(List continued on next page.)

FOREIGN PATENT DOCUMENTS

| | | | |
|---|---|---|---|
| 1077842 | 8/1976 | Canada .......... | A61K 9/50 |
| 0 000 667 A1 | 2/1979 | European Pat. Off. .......... | A61K 9/50 |
| 0 036 145 A1 | 9/1981 | European Pat. Off. .......... | A61K 31/62 |
| 0 068 314 | 1/1983 | European Pat. Off. .......... | A61K 31/16 |
| 0 105 804 | 4/1984 | European Pat. Off. .......... | C12N 15/00 |
| 0 130 162 A2 | 1/1985 | European Pat. Off. .......... | B01J 13/02 |
| 0 170 540 A1 | 2/1986 | European Pat. Off. .......... | A61K 9/52 |
| 0 342 054 A2 | 11/1989 | European Pat. Off. .......... | A61K 7/06 |
| 0 342 056 A2 | 11/1989 | European Pat. Off. .......... | A61K 7/06 |
| 0 365 183 | 4/1990 | European Pat. Off. .......... | A61K 31/18 |
| 0 366 277 | 5/1990 | European Pat. Off. .......... | A61K 9/107 |
| 0 418 642 | 3/1991 | European Pat. Off. .......... | A61K 37/30 |
| 0 448 057 | 9/1991 | European Pat. Off. .......... | C12P 21/08 |
| 0 452 161 | 10/1991 | European Pat. Off. .......... | A61K 7/48 |
| 0 459 795 | 12/1991 | European Pat. Off. .......... | A61K 37/02 |

(List continued on next page.)

OTHER PUBLICATIONS

Airaudo, C.B. et al. (1987) *Journal of Food Science*, vol. 52(6), pp. 1750–1752.

Andini, S. et al. (1975) *Origins of Life*, vol. 6, pp. 147–153.

Brooke, S. 1 et al. (1977) *BioSystems*, vol. 9, pp. 1–22.

Chen et al. (1975) "Evidence for Hemiacetal Formation", *Biochemistry*, vol. 18, No. 5, pp. 921–925.

Davis et al. (1983) "Leucinal Inhibits . . . ", *Pharmacology Biochemistry Behavior*, vol. 19, pp. 791–794.

Dose, K. (1974) *Origins of Life*, vol. 5, pp. 239–252.

Fasman et al. (1964) *Biochemistry*, vol. 3, No. 11, pp. 1665–1674.

Fox, S.W. et al. (1976) *BioSystems*, vol. 8, pp. 40–44.

Fox, S.W. et al., *Molecular Evolution and the Origin of Life*, Maxel Decker, New York (1977).

Fox, S.W. et al. (1968) *Biochim. Biophys. Acta*, vol. 160, pp. 246–249.

Fox, S.W. (1976) *Origins of Life*, vol. 7, pp. 49–68.

Fox, S.W. (1980) *Naturwissenschaften*, vol. 67, pp. 378–383.

(List continued on next page.)

*Attorney, Agent, or Firm—*

*Primary Examiner*—Gary Geist
*Assistant Examiner*—Brian J. Davis Darby & Darby

[57] ABSTRACT

Carrier compounds and compositions therewith which are useful in the delivery of active agents are provided. Methods of administration and preparation are provided as well.

31 Claims, No Drawings

U.S. PATENT DOCUMENTS

| | | | |
|---|---|---|---|
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,457,907 | 7/1984 | Porter | 424/7.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,683,092 | 7/1987 | Tsang | 264/4.3 |
| 4,690,786 | 9/1987 | Ninomiya et al. | 264/4.6 |
| 4,692,284 | 9/1987 | Braden | 264/4.3 |
| 4,692,433 | 9/1987 | Hostetler et al. | 514/12 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/19 |
| 4,908,233 | 3/1990 | Takizawa et al. | 427/213.35 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/497 |
| 5,023,374 | 6/1991 | Simon | 564/152 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/401 |
| 5,271,961 | 12/1993 | Mathiowitz et al. | 427/213.31 |
| 5,278,148 | 1/1994 | Branca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,377 | 2/1995 | Chagnon et al. | 424/450 |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,439,686 | 8/1995 | Desai et al. | 424/451 |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,474,997 | 12/1995 | Gray et al. | 514/252 |
| 5,536,813 | 7/1996 | Charpenel et al. | 530/324 |
| 5,540,939 | 7/1996 | Milstein et al. | 424/491 |
| 5,541,155 | 7/1996 | Leone-Bay et al. | 514/2 |
| 5,578,323 | 11/1996 | Milstein et al. | 424/499 |
| 5,601,846 | 2/1997 | Milstein et al. | 424/499 |
| 5,629,020 | 5/1997 | Leone-Bay et al. | 424/489 |
| 5,643,957 | 7/1997 | Leone-Bay et al. | 514/563 |
| 5,650,386 | 7/1997 | Leone-Bay et al. | 514/2 |
| 5,665,700 | 9/1997 | Cho et al. | 514/2 |
| 5,667,806 | 9/1997 | Kantor | 424/484 |
| 5,693,338 | 12/1997 | Milstein . | |
| 5,705,529 | 1/1998 | Matyus et al. . | |
| 5,709,861 | 1/1998 | Santiago et al. . | |
| 5,714,167 | 2/1998 | Milstein et al. . | |
| 5,750,147 | 5/1998 | Kantor . | |

FOREIGN PATENT DOCUMENTS

| | | | |
|---|---|---|---|
| 0 467 389 | 1/1992 | European Pat. Off. | A61K 9/52 |
| 0 490 549 A1 | 6/1992 | European Pat. Off. | A61K 47/12 |
| 0 517 211 A1 | 9/1992 | European Pat. Off. | A61K 47/12 |
| 0 616 799 A1 | 9/1994 | European Pat. Off. | A61K 7/00 |
| 2 565 102 | 12/1985 | France | A61K 9/52 |
| 2 424 169 | 12/1974 | Germany | A61K 9/00 |
| 2 343 037 | 3/1975 | Germany . | |
| 3 612 102.9 | 10/1986 | Germany | C07K 15/00 |
| 71258/2 | 12/1987 | Israel . | |
| 56-68612 | 6/1981 | Japan | A61K 31/19 |
| 58-35111 | 3/1983 | Japan | A61K 9/66 |
| 6-107682 | 4/1994 | Japan . | |
| 929401 | 6/1963 | United Kingdom . | |
| 1 075 952 | 8/1967 | United Kingdom . | |
| 1 236 885 | 6/1971 | United Kingdom . | |
| 1 567 763 | 5/1980 | United Kingdom | A61K 9/22 |
| 2 095 994 | 10/1982 | United Kingdom | A61K 9/00 |
| WO 85/00105 | 1/1985 | WIPO | A61K 9/52 |
| WO 85/00110 | 1/1985 | WIPO | A61K 47/00 |
| WO 85/00809 | 2/1985 | WIPO | C07D 233/64 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 9/107 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |
| WO 85/02772 | 7/1995 | WIPO | A61K 49/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO | A61K 9/16 |
| WO 96/12474 | 5/1996 | WIPO | A61K 9/16 |
| WO 96/12475 | 5/1996 | WIPO | A61K 9/16 |
| WO 96/21464 | 7/1996 | WIPO | A61K 39/00 |

| | | | |
|---|---|---|---|
| WO 96/30036 | 10/1996 | WIPO | A61K 38/00 |
| WO 96/33699 | 10/1996 | WIPO | A61K 9/16 |
| WO 96/39835 | 12/1996 | WIPO | A01N 43/50 |
| WO 96/40070 | 12/1996 | WIPO | A61K 9/14 |
| WO 96/40076 | 12/1996 | WIPO | A61K 9/16 |
| WO 97/10197 | 3/1997 | WIPO | C07C 51/10 |
| WO 97/31938 | 9/1997 | WIPO | C07K 5/00 |
| WO 97/36480 | 10/1997 | WIPO | A01N 37/12 |
| WO 97/47288 | 12/1997 | WIPO . | |

OTHER PUBLICATIONS

Fox, S.W. et al. (1960) *Archives of Biochemistry and Biophysics*, vol. 86, pp. 281–285.
Fox, S.W. et al. (1974) *Origins of Life*, vol. 5, pp. 227–237.
Fox, S.W. (1984) *Origins of Life*, vol. 14, pp. 485–488.
Gol'dovskii, A.M. (1978) *Zhurnal Evolyutsionnoi Biokhimii i Fiziologii*, vol. 14(6), pp. 437–439.
Gurrieri, S. et al. (1973) *Thermochimica Acta*, vol. 7, pp. 231–239.
Harada, K. et al. (1979) *BioSystems*, vol. 11, pp. 47–53.
Harada et al., (1960) *Archives of Biochemistry and Biophysics*, vol. 86, pp. 274–280.
Heinrich, M.R. et al. (1969) *Archives of Biochemistry and Biophysics*, vol. 130, pp. 441–448.
Heinz, B. et al. (1981) *BioSystems*, vol. 14, pp. 33–40.
Hennon, G. et al. (1975) *Biochimie*, vol. 57, pp. 1395–1396.
Hsu, L.L. et al. (1976) *BioSystems*, vol. 8, pp. 89–101.
Hsu, L.L. et al. (1971) *Currents in Modern Biology*, vol. 4, pp. 12–25.
Ishima, Y. et al. (1981), *BioSystems*, vol. 14, pp. 243–251.
Jackson et al. (1991) "Pharmacological . . . ", *J. Pharm. & Exp. Thera.*, vol. 261, No. 1, pp. 546–552.
Jungck, J.R. et al. (1973) *Naturwissenschaften*, vol. 60, pp. 425–427.
Kokufuta, E. et al. (1984) *BioSystems*, vol. 16, pp. 175–181.
Krampitz, G. et al. (1967) *Naturwissenschaften*, pp. 516–517.
Lacey, Jr., J.C. et al. (1979) *BioSystems*, vol. 11, pp. 9–17.
Lacey, Jr., J.C. et al. (1979) *BioSystems*, vol. 11, pp. 1–7.
Martinez Luque–Romero, M. et al. (1986) *BioSystems*, vol. 19, pp. 267–272.
Masinovsky, Z. et al. (1989) *BioSystems*, vol. 22, pp. 305–310.
Matsuno, K. (1982) *BioSystems*, vol. 15, pp. 1–11.
Matsuno, K. (1984) *BioSystems*, vol. 17, pp. 11–14.
Matsuno, K. (1981) *BioSystems*, vol. 14, pp. 163–170.
McAlhaney, W.W. et al. (1976) *BioSystems*, vol. 8, pp. 45–50.
Melius, P. et al. (1987) *BioSystems*, vol. 20, pp. 213–217.
Melius, P. et al. (1975) *Bioorganic Chemistry*, vol. 4, pp. 385–391.
Melius, P. (1979) *BioSystems*, vol. 11, pp. 125–132.
Miquel, J. et al. (1971) *Currents in Modern Biology*, vol. 3, pp. 299–306.
Nakashima, T. et al. (1980) *J. Mol. Evol.*, vol. 15, pp. 161–168.
Nakashima, T. et al. (1981) *BioSystems*, vol. 14, pp. 151–161.
Novak, V.J.A. (1984) *Origins of Life*, vol. 14, pp. 513–522.
Olafsson, P.G. et al. (1971) *Polymer Letters*, vol. 9, pp. 521–528.
Phillips, R.D. et al. (1974) *Int. J. Peptide Protein Res.*, vol. 6, pp. 309–319.
Przybylski, A.T. et al. (1982) *Die Naturwissenschaften*, vol. 69, pp. 561–563.

Przybylski, A.T. et al. (1984) *Applied Biochemistry and Biotechnology*, vol. 10, pp. 301–307.
Przybylski, A.T. (1985) *BioSystems*, vol. 17, pp. 281–288.
Rohlfing, D.L. (1975) *Origins of Life*, vol. 6, pp. 203–209.
Rohlfing, D.L. (1970) *Science*, vol. 169, pp. 998–1000.
Rohlfing, D.L. (1967) *Archives of Biochemistry and Biophysics*, vol. 118, pp. 468–474.
Rohlfing, D.L. et al. *Catalytic Activities of Thermal Polyanhydro–α–Amino Acids*, pp. 373–418, 1969.
Rohlfing, D.L. et al. (1976) *BioSystems*, vol. 8, pp. 139–145.
Ryan, J.W. et al. (1973) *BioSystems*, vol. 5, pp. 115–118.
Saunders, M.A. et al. (1974) *BioSystems*, vol. 6, pp. 81–92.
Snyder, W.D. et al. (1975) *BioSystems*, vol. 7, pp. 222–229.
Sokol, P.E. (1974) *Journal of the American Oil Chemists'Society*, vol. 52, pp. 101–102.
Vaughan, G. et al. (1987) *BioSystems*, vol. 20, pp. 219–223.
Vol'kenshtein, M.V. (1989) *Molekulyarnaya Biologiya*, vol. 23(1), pp. 23–37.
Waehneldt, T.V. et al. (1968) *Biochim. Biophys. Acta*, vol. 160, pp. 239–245.
Williams et al. (1991) *J. Biol. Chem.*, vol. 266, No. 8, pp. 5182–5190.
Yuki, A. et al. (1969) *Biochemical and Biophysical Research Communications*, vol. 36(4), pp. 657–663.
Zulaski et al. (1983) "New Carboxyalkyl Inhibitors of Brain Enkenphalinase", *J. Med. Chem.*, 26, pp. 60–65.
(1985) *Chemical Abstracts*, vol. No. 105(1), Abstract No. 12027p.
(1985) *Chemical Abstracts*, vol. No. 102(6), Abstract No. 50870d.
*Chemical Abstract*, vol. 80(9) Abst. No. 52392a.
Bergeron, Raymond J., et al. (1994) "Macromolecular Self–Assembly of Diketopiperazine Tetrapeptides", *Journal of the American Chemical Society*, vol. 116, pp. 8479–8484.
Bergeron, Raymond, J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.
Bergeron, Raymond et al., "A Comparative Evaluation of Iron Clearance Models", *Annals New York Academy of Sciences*, pp. 278–393, Mar. 13–15, 1990.
Andriuoli, G., et al. (1990), *Haemostasis* 20 (suppl. 1):154–158.
Caramazza, I., et al. (1991), *Thrombosis Research* 62:785–789.
Guarini, S., et al. (1983), *Experimentia* 41:350–352.
Guarini, S., et al. (1985), *Pharmacological Research Communications* 17(8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research*, vol. 23, No. 4, part 2, p. 570A, col. 1, abstract No. 2209.
Bernstein (1985), *Chest* 87(1):68S–73S.
Damge et al. (1988), *Diabetes* 37:246–251.
*Chemical Abstracts*:83 184360k, (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah,* Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater.,* 20 (1993), Controlled Release Society, Inc.

X. Ma, et al., *Proceed. Intern. Symp. Control. Rel. Bioact. Mater.,* 20 (1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.,* 20 (1993), Controlled Release Society, Inc.

Presented at *"IBC Rational Drug Design Conference",* San Diego, Calif.—Dec. 1994.

Leone–Bay et al., Presented at *"Winter Conference on Medicinal and Bioorganic Chemistry"* Steamboat Springs, Colorado—Feb. 1995 Microsphere Formation and Drug Delivery in a Series of Derivatized Amino Acids.

Santiago et al., *Pharm. Res.* 11: 1994, p. S–298 "Oral Delivery of Heparin Microspheres made with Modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts.* AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.,* 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.,* 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.,* 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.,* 19 (1992), Controlled Release Society, Inc. pp. 516–517.

Doris K. Chiappetta, *Eastern Analytical Symposium,* Nov. 17, 1992 "Solutions for Problems in Bioanalysis".

Elizabeth A. Harris. M.S., *Eastern Analytical Symposium,* Nov. 17, 1992 "Solutions for Problems in Bioanalysis".

*AAPS 6TH Ann. Meeting and Expo.,* "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond,* Jan. 17–22, 1993.

Xinghang Ma, et al. "Stability Study of Drug–loaded Proteinoid Microsphere Formulations during Freeze–drying" *Journal of Drug Targeting,* 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems,* Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology,* 1993: 14 pp. 29–39 "Physical barriers to drug delivery in tumors".

V. Hird et al, *Genes and Cancer,* edited by Desmond Carney & Karol Sikora, pp. 183–189, Immunotherapy with Monoclonal Antibodies.

Michael E. Osband et al., *Immunology Today,* vol. 11, No. 6 1990, pp. 193–195, "Problems in the investigational study and clinical use of cancer immunotherapy".

William J. Harris, *Tibtech* Feb. 1993 vol. 11, pp. 42–44 "Therapeutic antibodies—the coming of age".

Thomas A. Waldmann, *Science,* Jun. 21, 1991, 252:1657–1662, "Monoclonal Antibodies in Diagnosis and Therapy".

*Chemical Abstracts,* 76(14):72994u, (1971).

*Chemical Abstracts,* 84(7):44660d, (1975).

*Chemical Abstracts,* 86(16):107529g, (1976).

*Chemical Abstracts,* 112(15):134663h, (1989).

*Chemical Abstracts,* 114(22):214519x, (1990).

J. Györe et al., *Thermal Analysis,* vol. 2—Proceeding Fourth ICTA Budapest 1974, pp. 387–394.

*Chemical Abstracts,* 99(19) 158832b, (1982).

*Derwent Abstracts,* JP 67008622, (1967).

*Journal of Medicinal Chemistry,* vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry,* vol. 38, No. 21, pp. 4263–4269, (1995), "N–Acylated α–Amino Acids as Novel Oral Delivery Agents for Proteins".

*The Extra Pharmacopoeia,* Thirtieth Edition, pp. 325–326, (1993).

Stephen J. Douglas et al., *Chemistry and Industry,* vol. 22:748–751, 1985.

C.A. Finch, *Chemistry and Industry,* vol. 22:752–756, 1985.

John A. Butera et al., *J. Med. Chem.,* vol. 34:3212–3228, 1990.

Madeline G. Cimini et al., *Ann. Report in Med Chem.,* vol. 27:89–98., 1992.

Bernadette Earley et al., *Brain Research,* vol. 546:282–286, 1991.

John W. Ellingboe et al., *J. Med Chem.,* vol. 35:705–716, 1992.

William C. Lumma et al., *J. Med Chem.,* vol. 30:758–763, 1987.

Joseph J. Lynch et al., *J. of Pharm. and Exp. Therap.,* vol. 269:541–554, 1994.

Kiyoshi Matsuno et al., *Brain Research,* vol. 575:315–319, 1992.

Thomas K. Morgan et al., *J. Med. Chem.,* vol. 33:1091–1097, 1990.

Hitoshi Oinuma et al., *J. Med Chem.,* vol. 33:903–905, 1990.

Tadimeti S. Rao et al., *Molecular Pharmacology,* vol. 37:978–982, 1990.

Asaji Kondo, *Microcapsule Processing and Technology,* pp. 154–165, 1979.

G. Pastores et al., *J. Liquid Chromatography,* 18(15):3049–3059, 1995.

D. Sinha et al., *J. Bio. Chem.,* 260(19):10714–10719. 1985.

E. Franssen et al., *J. Med. Chem.,* 35:1246–1259, 1992.

*Chemical Abstracts,* 99(23):191473h, Dec. 5, 1983.

R. Langer, *Science,* 249:1528, Sep. 28, 1990.

M. Alonso et al., *Vaccine,* 12:299, 1994.

A. Leone–Bay et al., *J. Med. Chem.,* 39:2571–2578, 1996.

R. Thompson, *Biochemistry,* 12:47–51, 1973.

S. Thompson, *J. Med. Chem.,* abstract, 86:174780, 1986.

COMPOUNDS AND COMPOSITIONS FOR DELIVERING ACTIVE AGENTS

FIELD OF THE INVENTION

The present invention relates to compounds for delivering active agents, and particularly biologically or chemically active agents. These compounds are used as carriers to facilitate the delivery of a cargo to a target. The carrier compounds are well suited to form non-covalent mixtures with biologically-active agents for oral administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers.

For example in the delivery to animals of biologically active or chemically active pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastro-intestinal (GI) tract, powerful digestive enzymes, and active agent impermeable gastro-intestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents.

SUMMARY OF THE INVENTION

Compounds and compositions which are useful in the delivery of active agents are provided. These compositions include at least one active agent, preferably a biologically or chemically active agent, and at least one of the following compounds 1–3, or salts thereof.

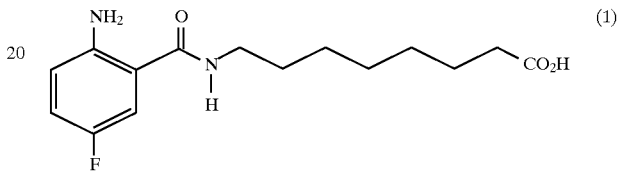

N-2(amino-5-fluorobenzoyl)-8-aminocaprylic acid

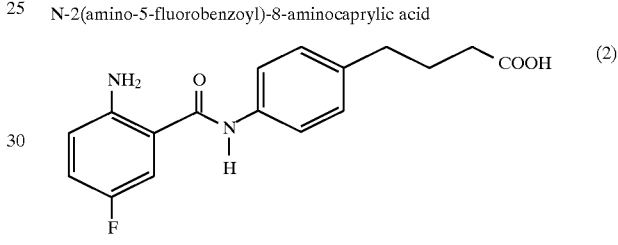

4-(N-(5-fluoro-2-aminobenzoyl)-4-aminophenyl)butyric acid

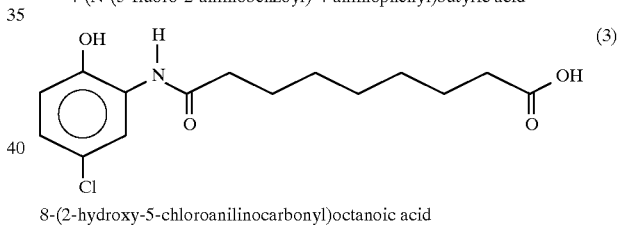

8-(2-hydroxy-5-chloroanilinocarbonyl)octanoic acid

Compositions comprising one or more carrier compounds discussed above and active agents are effective in delivering active agents to selected biological systems.

DETAILED DESCRIPTION OF THE INVENTION

The specific compositions of the present invention include an active agent and a carrier. These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds including, but not limited to, chickens; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Subcutaneous, sublingual, and intranasal coadministration of an active agent, such as, for example, recombinant human growth hormone (rhGH); salmon calcitonin; heparin, including, but not limited to, low molecular weight heparin; parathyroid hormone; and compounds in compositions as described herein result in an increased bioavailability of the active agent compared to administration of the active agent alone.

Active Agents

Active agents suitable for use in the present invention include biologically or chemically active agents, chemically active agents, including, but not limited to, fragrances, as well as other active agents such as, for example, cosmetics.

Biologically or chemically active agents include, but are not limited to, pesticides, pharmacological agents, and therapeutic agents. For example, biologically or chemically active agents suitable for use in the present invention include, but are not limited to, peptides, and particularly small peptides; hormones, and particularly hormones which by themselves do not or only a fraction of the administered dose passes through the gastro-intestinal mucosa and/or are susceptible to chemical cleavage by acids and enzymes in the gastro-intestinal tract; polysaccharides, and particularly mixtures of muco-polysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); parathyroid hormone; anti-microbials, including, but not limited to anti-fungal agents; or any combination thereof.

Carriers

Compounds 1–3 above have been found to act as carriers for the oral delivery of biologically or chemically active agents. Properties of compounds 1–3 are listed in Table 1, below.

acids. See *Chambers Biological Dictionary*, editor Peter M. B. Walker, Cambridge, England: Chambers Cambridge, 1989, page 215. Special mention is made of di-peptides, tri-peptides, tetra-peptides, and penta-peptides.

Salts such as, for example, sodium salt of these carrier compounds can be used as well.

These carrier compounds are derived from amino acids and can be prepared as shown in the Examples below. See also, U.S. patent application Ser. Nos. 60/017,902, filed Mar. 29, 1996; 08/414,654, filed Mar. 31, 1995; 08/335,148, filed Oct. 25, 1994; and 60/003,111, filed Sep. 1, 1995.

The carrier compound may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0–500 mM sodium chloride gradient is employed.

Delivery Systems

The compositions of the present invention may include one or more active agents.

In one embodiment, compounds 1–3 or salts of compounds 1–3 or poly amino acids or peptides that include at least one of these compounds or salts may be used directly as a delivery carrier by simply mixing one or more compound or salt, poly amino acid, or peptide with the active agent prior to administration.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

TABLE 1

| | Carrier Properties | | | | | | | | |
|---|---|---|---|---|---|---|---|---|---|
| | Anal. Calculated For | | | | Found | | | | Melting | |
| Compound | C | H | N | S | C | H | N | S | Point (°C.) | Solubility |
| 1 | 60.79 | 7.14 | 9.45 | | 60.89 | 7.18 | 9.41 | | 108–109 | 200 mg/mL, slightly milky at pH = 8.7 |
| 2 | 64.55 | 5.42 | 8.86 | | 64.38 | 5.42 | 8.74 | | 165–168 | 200 mg/mL, milky suspension at pH = 8.44 |
| 3 | 57.42 | 6.42 | 4.46 | | 57.3 | 6.38 | 4.39 | | 119–120 | 200 mg/mL, soluble at pH = 8.28 |

These carrier compounds or poly amino acids and peptides which include these carriers, may be used to deliver active agents including, but not limited to, biologically or chemically active agents such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g. an ester, anhydride, or an anhydride linkage.

Peptides are two or more amino acids joined by a peptide bond. Peptides can vary in length from dipeptides with two amino acids to poly peptides with several hundred amino Stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent is an amount effective to accomplish the purpose of the particular active agent. The amount in the composition typically is a pharmacologically, biologically, therapeutically, or chemically effective amount. However, the amount can be less than a pharmacologically, biologically, therapeutically, or chemically effective amount when the composition is used in a dosage unit form, such as a capsule, a tablet or a liquid, because the dosage unit form may contain a multiplicity of carrier/biologically or chemically active agent compositions or may contain a divided pharmacologically, biologically, therapeutically, or chemically effective amount. The total effective amounts can then be administered in cumulative units containing, in total, pharmacologically, biologically, therapeutically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers provides extremely efficient delivery, particularly in oral, intranasal, sublingual, intraduodenal, or subcutaneous systems. Therefore, lower amounts of biologically or chemically active agent than those used in prior dosage unit forms or delivery systems can be administered to the subject, while still achieving the same blood levels and therapeutic effects.

The amount of carrier in the present composition is a delivery effective amount and can be determined for any particular carrier or biologically or chemically active agent by methods known to those skilled in the art.

Dosage unit forms can also include any of excipients; diluents; disintegrants; lubricants; plasticizers; colorants; and dosing vehicles, including, but not limited to polyethylene glycol, polyvinyl pyrrolidine, water, 1,2-propane diol, ethanol, olive oil, or any combination thereof.

The delivery compositions of the present invention may also include one or more enzyme inhibitors. Such enzyme inhibitors include, but are not limited to, compounds such as actinonin or epiactinonin and derivatives thereof. These compounds have the formulas below:

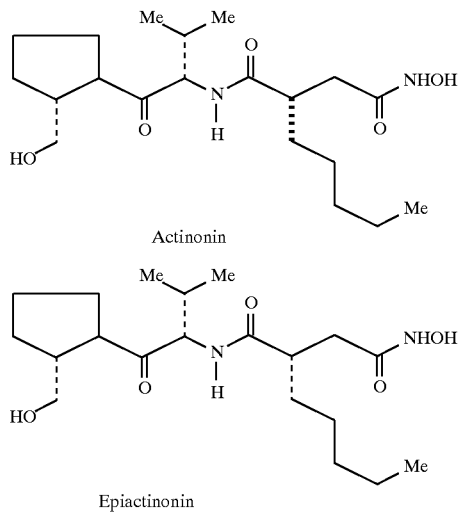

Actinonin

Epiactinonin

Derivatives of these compounds are disclosed in U.S. Pat. No. 5,206,384. Actinonin derivatives have the formula:

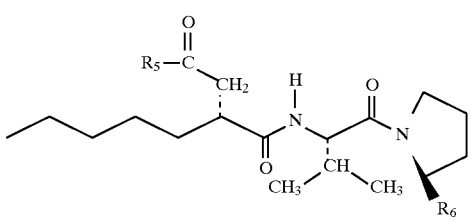

wherein $R^5$ is sulfoxymethyl or carboxyl or a substituted carboxy group selected from carboxamide, hydroxyaminocarbonyl and alkoxycarbonyl groups; and $R^6$ is hydroxyl, alkoxy, hydroxyamino or sulfoxyamino group. Other enzyme inhibitors include, but are not limited to, aprotinin (Trasylol) and Bowman-Birk inhibitor.

The compounds and compositions of the subject invention are useful for administering biologically or chemically active agents to any animals such as birds; mammals, such as primates and particularly humans; and insects. The system is particularly advantageous for delivering chemically or biologically or chemically active agents which would otherwise be destroyed or rendered less effective by conditions encountered before the active agent its target zone (i.e. the area in which the active agent of the delivery composition are to be released) and within the body of the animal to which they are administered. Particularly, the compounds and compositions of the present invention are useful in orally administering active agents, especially those which are not ordinarily orally deliverable.

DESCRIPTION OF THE PREFERRED EMBODIMENTS

The following examples illustrate the invention without limitation. All parts are given by weight unless otherwise indicated.

EXAMPLE 1

Carrier Preparation

General Preparations of Carriers. The following procedures were used to prepare the compounds described herein.

Preparation of Compound 1.

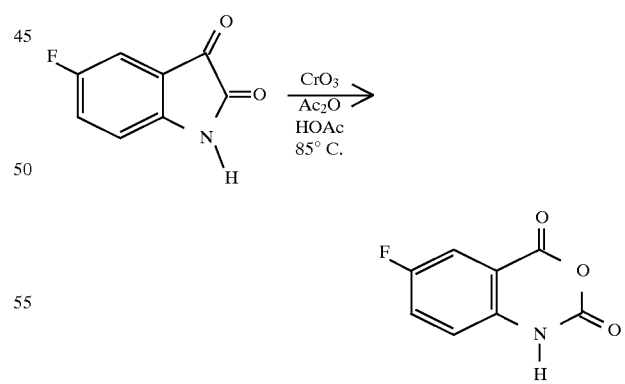

Preparation of 5-Fluoroisatoic Anhydride. Acetic anhydride (90.0 mL), 5-fluoroisatin (20.62 g, 0.125 mmol, 1.00 eq), and acetic acid (90 mL) were added to a 250 mL, three neck flask fitted with a magnetic stir bar and a condenser. The flask was placed in a water bath and heated to 85° C. Chromium (VI) oxide (20.36 g, 0.204 mol, 1.63 eq) was added in small portions (0.5 g size) over 40 min to the red solution. The reaction mixture was stirred for an additional 15 min and cooled to 10° C. in an ice bath. The solid that formed was isolated by filtration. Washing with 400 mL of water removed most of the green color. The solid was taken up in 300 mL of 2:1 acetic acid/water, refiltered, and dried overnight in a 50° C. vacuum oven. The 5-fluoroisatoic anhydride was isolated as a bright yellow solid (14.45 g, 64%).

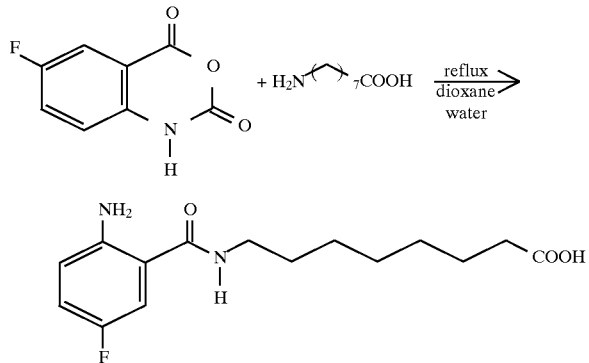

Preparation of N-(2-Amino-5-fluorobenzoyl)-8-aminocaprylic Acid (E-815). A 50% (by weight) solution of potassium carbonate (11.2 mL, 16.8 mmol, 1.02 eq), 8-aminocaprylic acid (9.5 g, 59.7 mmol, 1.00 eq), 5-fluoroisatoic anhydride (10.82 g, 59.7 mmol, 1.00 eq), dioxane (40 mL), and water (5 mL) were added to a 100 mL round bottom flask equipped with a magnetic stir bar and a condenser. The red cloudy mixture was heated to 90° C. for 2 hours (at which time the reaction was determined, by HPLC, to have finished). The deep purple solution was cooled to 25° C. and acidified to pH=4.0 with 3% (by vol.) aqueous hydrochloric acid. The dark precipitate which formed was isolated by filtration. The solid was recrystallized from 50 mL of 65% ethanol-water, recovered by filtration, and dried over 6 hours in a 50° C. vacuum oven. The N-(2-amino-5-fluorobenzoyl) -8-aminocaprylic acid was isolated as a light yellow solid (11.86 g, 67%), mp=108°–109° C.

Preparation of Compound 2.

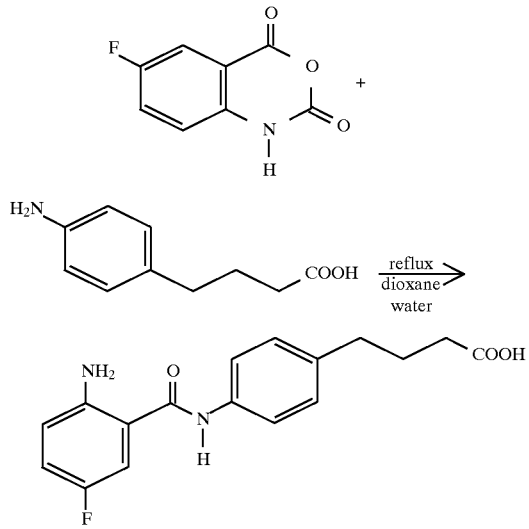

Preparation of 4-(N-Amino-5-fluorobenzoyl)-4-aminophenyl)butyric Acid. 5-fluoroisatoic anhydride (7.10 g, 39.2 mmol, 1.00 eq), 4-(4-aminophenyl)butyric acid (7.02 g, 39.2 mmol, 1.00 eq), dioxane (80 mL), and water 20 mL) were added to a 100 mL round bottom flask equipped with a magnetic star bar and a condenser. The red cloudy mixture was heated to 90° C. for 6 hours (at which time the reaction was determined, by HPLC, to have finished). The reaction mixture was cooled to 30° C. and filtered to remove a small amount of solid. The filtrate was concentrated to an orange brown solid. The solid was recrystallized from 50 mL of ethanol (1st crop) and 80% ethanol-water (2nd crop), recovered by filtration, and dried over 6 hours in a 50° C. vacuum oven. The 4-(N-(2-amino-5-fluorobenzoyl)-4-aminophenyl) butyric was isolated as a light tan solid (7.11 g, 57%), mp=169°–170° C.

Preparation of Compound 3.

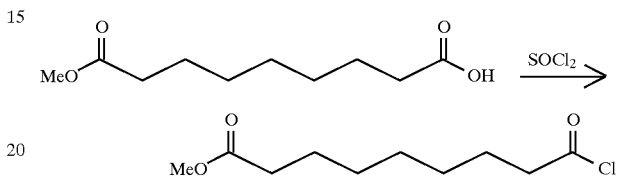

Methyl Azeloyl Chloride. A mixture of methyl hydrogen azelate (14.68 g, 72.58 mmol) and thionyl chloride (5.6 mL, 76.75 mmol) was refluxed for 3 h. The excess thionyl chloride was removed in vacuo. The residue was distilled under reduced pressure. The fractions between 130°–134° C. at 3.5 mm/Hg were combined yielding methyl azeloyl chloride as a colorless oil (14 g, 87%).

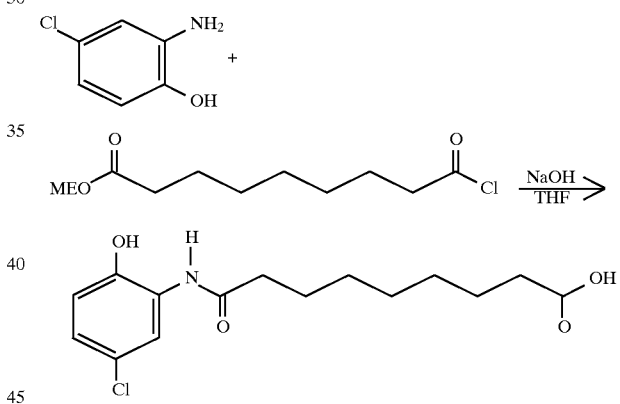

Preparation of 8-(2-hydroxy-5-chloroanilinocarbonyl) octanoic acid. To a cold solution of 2-amino-4-chlorophenol (2.56 g, 17.83 mmol) in tetrahydrofuran (40 mL) was added a solution of hydroxide (0.72 g, 18 mmol) in water (15 mL). The mixture was stirred at 0° C. for 5 min. A solution of methyl azeloyl chloride (3.9 g, 17.67 mmol) in tetrohydrofuran (10 mL) was added dropwise to this mixture. The resulting mixture was stirred at 0° C., then gradually warmed to room temperature, and stirred at room temperature overnight. A solution of sodium hydroxide (2N, 25 mL) was added to the reaction mixture. The mixture was stirred at room temperature and monitored by TLC. When the starting material was no longer visible, the reaction mixture was concentrated in vacuo. The residue was acidified to pH 2, and the precipitated solid was collected by filtration. This crude product was dissolved in methanol (50 mL), decolorized with activated charcoal, and filtered. A small amount of acetone and water was added to the filtrate, and the mixture refrigerated overnight. A solid was formed, collected by filtration, washed with water, and dried to give the product as a pale yellow, crystalline solid (3.0 g, 54%); mp 117°–118° C.; $^1$H NMR (DMSO-d$_6$) δ7.96 (d, J=2.5 Hz, 1H), 6.95 (dd, J=8.6, 2.6 Hz, 1H), 6.85 Hz, 1H), 2.39 (t, J=7.3 Hz, 2H), 2.19 (t, J=7.3 Hz, 2H), 1.40–1,61 (m, 4H), 1.20–1.35 (m, 6H). Anal. Calcd for C$_5$H$_{20}$ClNO$_4$:C, 57.42; H, 6.42; N, 4.46. Found: C, 57.24; H, 6.30; N, 4.41.

EXAMPLE 2

Parathyroid Hormone Dosing Solutions

Oral gavage ("PO") dosing solutions containing 300 mg/kg of carrier compound 1, 2 or 3 and 100 μg/kg of parathyroid hormone in water were prepared. The dosing solution are designated P- carrier number - DS.

EXAMPLE 3

In vivo Parathyroid Hormone Delivery

Male Sprague-Dawley rats weighing between 200–250g were fasted for 24 hours and were administered ketamine (44 mg/kg) and chlorpromazine (1.5 mg/kg) 15 minutes prior to dosing. The rats were administered one of dosing solutions P-1-DS, P-2-DS, or P-3-DS by oral gavage ("PO"). Blood samples were collected serially from the tail artery for serum determination of parathyroid hormone concentration. Serum parathyroid hormone concentrations were quantified by a parathyroid hormone immunoaccuracy test host.

Results are illustrated in Table 2, below.

TABLE 2

In vivo Parathyroid Hormone Delivery

| Dosing Solution | Cmax (pg/ml) |
| --- | --- |
| P-1-DS | 11.93 |
| P-1-DS | 19.75 |
| P-1-DS | 38.37 |
| Average P-1-DS | 23.35 |
| P-2-DS | 36.05 |
| P-2-DS | 222.16 |
| P-2-DS | 51 |
| Average P-2-DS | 103.1 |
| P-3-DS | 53.03 |
| P-3-DS | 616.61 |
| P-3-DS | 44.33 |
| Average P-3-DS | 237.99 |

EXAMPLES 4

Recombinant Human Growth Hormone Dosing Solutions

Oral gavage dosing solutions containing 300 mg/kg of carrier compound 2 and 6 mg/kg of rHGH or 25 mg/kg of carrier 3 and 1 mg/kg of rHGH, both in phosphate buffer, were prepared.

The dosing solutions are designated R- carrier number - DS.

EXAMPLE 5

In Vivo Recombinant Human Growth Hormone Delivery

Male Sprague-Dawley rats weighing 200–250g were fasted for 24 hours and administered ketamine (44 mg/kg) and chlorpromazine (1.5 mg/kg) 15 minutes prior to dosing. The rats were administered one of the dosing solutions R-2-DS or R-3-DS by oral gavage. Blood samples were collected serially from the tail artery for determination of serum rHGH concentrations. Serum rHGH concentrations were quantified by an rHGH immunoassay test kit.

Results are illustrated in Table 3, below.

TABLE 3

In Vivo Recombinant Human Growth Hormone Delivery

| Dosing Solution | Cmax (ng/ml) |
| --- | --- |
| R-2-DS | 115.7 |
| R-3-DS | 86.37 |
| R-3-DS | 123.34 |
| Average R-3-DS | 104.9 |

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A composition comprising:
(A) at least one active agent; and
(B) at least one carrier selected from the group consisting of

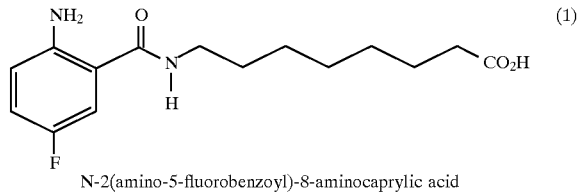

N-2(amino-5-fluorobenzoyl)-8-aminocaprylic acid

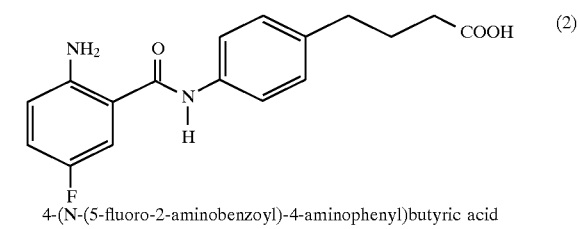

4-(N-(5-fluoro-2-aminobenzoyl)-4-aminophenyl)butyric acid

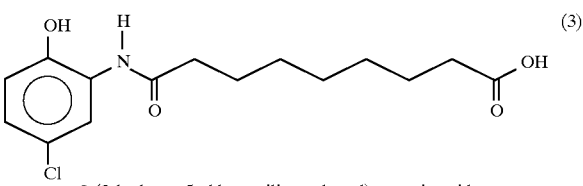

8-(2-hydroxy-5-chloroanilinocarbonyl)octanoic acid and a salt of any of the foregoing.

2. A composition as defined in claim 1, wherein said active agent is selected from the group consisting of a biologically active agent, a chemically active agent, or a combination thereof.

3. A composition as defined in claim 2, wherein said biologically active agent comprises at least one peptide, mucopolysaccharide, carbohydrate, or lipid.

4. A composition as defined in claim 2, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

5. A composition as defined in claim 4, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

6. A composition as defined in claim 1, wherein said carrier comprises a poly(amino acid).

7. A composition as defined in claim 1, wherein said carrier comprises a polypeptide.

8. A dosage unit form comprising
(A) a composition as defined in claim 1; and
(B) (a) an excipient
   (b) a diluent,
   (c) a disintegrant,
   (d) a lubricant,
   (e) a plasticizer,
   (f) a colorant,
   (g) a dosing vehicle, or
   (h) any combination thereof.

9. A composition as defined in claim 8, wherein said active agent is selected from the group consisting of a biologically active agent, a chemically active agent, or a combination thereof.

10. A composition as defined in claim 9, wherein said biologically active agent comprises at least one peptide, mucopolysaccharide, carbohydrate, or lipid.

11. A composition as defined in claim 9, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

12. A composition as defined in claim 11, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

13. A dosage unit form comprising
(A) a composition as defined in claim 6; and
(B) (a) an excipient
   (b) a diluent,
   (c) a disintegrant,
   (d) a lubricant,
   (e) a plasticizer,
   (f) a colorant,
   (g) a dosing vehicle, or
   (h) any combination thereof.

14. A composition as defined in claim 13, wherein said active agent is selected from the group consisting of a biologically active agent, a chemically active agent, or a combination thereof.

15. A composition as defined in claim 14, wherein said biologically active agent comprises at least one peptide, mucopolysaccharide, carbohydrate, or lipid.

16. A composition as defined in claim 14, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

17. A composition as defined in claim 16, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

18. A dosage unit form comprising
(A) a composition as defined in claim 7; and
(B) (a) an excipient
   (b) a diluent,
   (c) a disintegrant,
   (d) a lubricant,
   (e) a plasticizer,
   (f) a colorant,
   (g) a dosing vehicle, or
   (h) any combination thereof.

19. A composition as defined in claim 18, wherein said active agent is selected from the group consisting of a biologically active agent, a chemically active agent, or a combination thereof.

20. A composition as defined in claim 19, wherein said biologically active agent comprises at least one peptide, mucopolysaccharide, carbohydrate, or lipid.

21. A composition as defined in claim 19, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

22. A composition as defined in claim 21, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

23. A dosage unit form as defined in claim 8, comprising a tablet, a capsule, or a liquid.

24. A dosage unit form as defined in claim 23, wherein said dosing vehicle is selected from the group consisting of water, 1,2-propane diol, ethanol, or any combination thereof.

25. A dosage unit form as defined in claim 13, comprising a tablet, a capsule, or a liquid.

26. A dosage unit form as defined in claim 25, wherein said dosing vehicle is selected from the group consisting of water, 1,2-propane diol, ethanol, or any combination thereof.

27. A dosage unit form as defined in claim 18, comprising a tablet, a capsule, or a liquid.

28. A dosage unit form as defined in claim 27, wherein said dosing vehicle is selected from the group consisting of water, 1,2-propane diol, ethanol, or any combination thereof.

29. A method for administering a biologically-active agent to an animal in need of said agent, said method comprising administering orally to said animal a composition as defined in claim 2.

30. A compound selected from the group consisting of

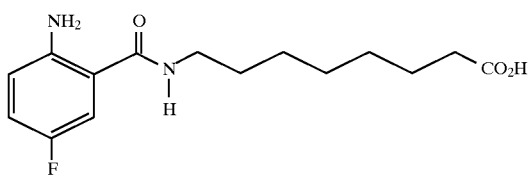

N-2(amino-5-fluorobenzoyl)-8-aminocaprylic acid (1)

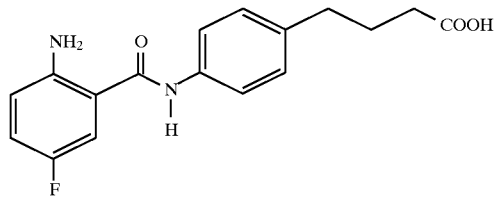

4-(N-(5-fluoro-2-aminobenzoyl)-4-aminophenyl)butyric acid (2)

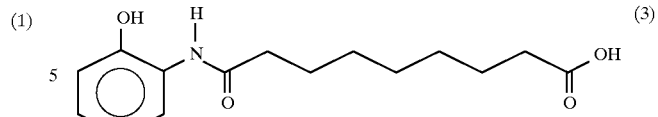

8-(2-hydroxy-5-chloroanilinocarbonyl)octanoic acid (3)

and a salt of any of the foregoing.

31. A method for preparing a composition, said method comprising mixing:

(A) at least one active agent;
(B) at least one compound as defined in claim 31; and
(C) optionally, a dosing vehicle.

* * * * *